US010605746B2

(12) United States Patent
Ramzan et al.

(10) Patent No.: US 10,605,746 B2
(45) Date of Patent: Mar. 31, 2020

(54) PLANT WATER SENSOR

(71) Applicant: UNITED ARAB EMIRATES UNIVERSITY, Al Ain (AE)

(72) Inventors: Rashad Ramzan, Al Ain (AE); Omar Farooq Sidiqui, Al Ain (AE); Muhammad Amin, Al Ain (AE); Nabil Bastaki, Al Ain (AE)

(73) Assignee: United Arab Emirates University, Al Ain (AE)

( * ) Notice: Subject to any disclaimer, the term of this patent is extended or adjusted under 35 U.S.C. 154(b) by 92 days.

(21) Appl. No.: 15/846,051

(22) Filed: Dec. 18, 2017

(65) Prior Publication Data

US 2019/0187072 A1    Jun. 20, 2019

(51) Int. Cl.
*G01N 22/04* (2006.01)
*G01N 33/00* (2006.01)
*G01R 27/26* (2006.01)

(52) U.S. Cl.
CPC ......... *G01N 22/04* (2013.01); *G01N 33/0098* (2013.01); *G01R 27/2623* (2013.01)

(58) Field of Classification Search
CPC ............................ G01N 22/04; G01N 33/0098
See application file for complete search history.

(56) References Cited

U.S. PATENT DOCUMENTS

| 4,789,820 | A | * | 12/1988 | Parrent, Jr. ............ G01N 21/86 324/640 |
| 5,039,947 | A | | 8/1991 | Kraszewski et al. |
| 5,666,061 | A | | 9/1997 | Assenheim |
| 6,407,555 | B2 | | 6/2002 | Joshi |

(Continued)

FOREIGN PATENT DOCUMENTS

| JP | 2005-292099 A | 10/2005 |
| KR | 2014-0082376 A | 7/2014 |

OTHER PUBLICATIONS

Sarabandi et al., "Microstrip ring resonator for soil moisture measurements." IEEE transactions on geoscience and remote sensing 35.5 (1997): 1223-1231.
Kraszewski et al., "Microwave aquametry: an effective tool for nondestructive moisture sensing." Subsurface sensing technologies and applications 2.4 (2001): 347-362.

(Continued)

*Primary Examiner* — Noam Reisner
(74) *Attorney, Agent, or Firm* — Richard C. Litman; Nath, Goldberg & Meyer

(57) ABSTRACT

The plant water Anomalous Phase sensor can determine moisture levels in plant leaves, stems and wood. The sensors described include several embodiments of the sensor, all of which estimate moisture levels by determining changes in the phase spectrum of an anomalous-phase resonator. Two embodiments include a planar transmitting antenna array with two slightly detuned patch antennas and a detector. In a first embodiment, the detector is a dipole antenna centered and out of plane with the transmitting antenna array. In a second embodiment, the detector is a singular rectangular patch antenna coplanar with the transmitting antenna array. The third embodiment is similar to the second embodiment, but is formed on a flexible substrate, so that the sensor can be wrapped about a twig, branch or other plant structure, in a non-coplanar arrangement. To compensate for temperature affects, a reference sensor may be integrated with an active sensor.

13 Claims, 6 Drawing Sheets

(56) References Cited

U.S. PATENT DOCUMENTS

| | | |
|---|---|---|
| 7,560,937 B2 | 7/2009 | Bini et al. |
| 7,928,739 B2 | 4/2011 | Sherman et al. |
| 9,201,056 B2 | 12/2015 | Gordon et al. |
| 2012/0025848 A1 | 2/2012 | Hasch et al. |
| 2014/0320356 A1* | 10/2014 | Bishop .................. H01Q 1/287 343/705 |
| 2017/0131334 A1 | 5/2017 | Ramzan et al. |

OTHER PUBLICATIONS

Siddiqui et al., "A Non-Invasive Phase Sensor for Permittivity and Moisture Estimation Based on Anomalous Dispersion." Scientific Reports 6 (2016).

Ramzan et al., "A Complex Permittivity Extraction Method Based on Anomalous Dispersion." IEEE Transactions on Microwave Theory and Techniques 64.11 (2016): 3787-3796.

* cited by examiner

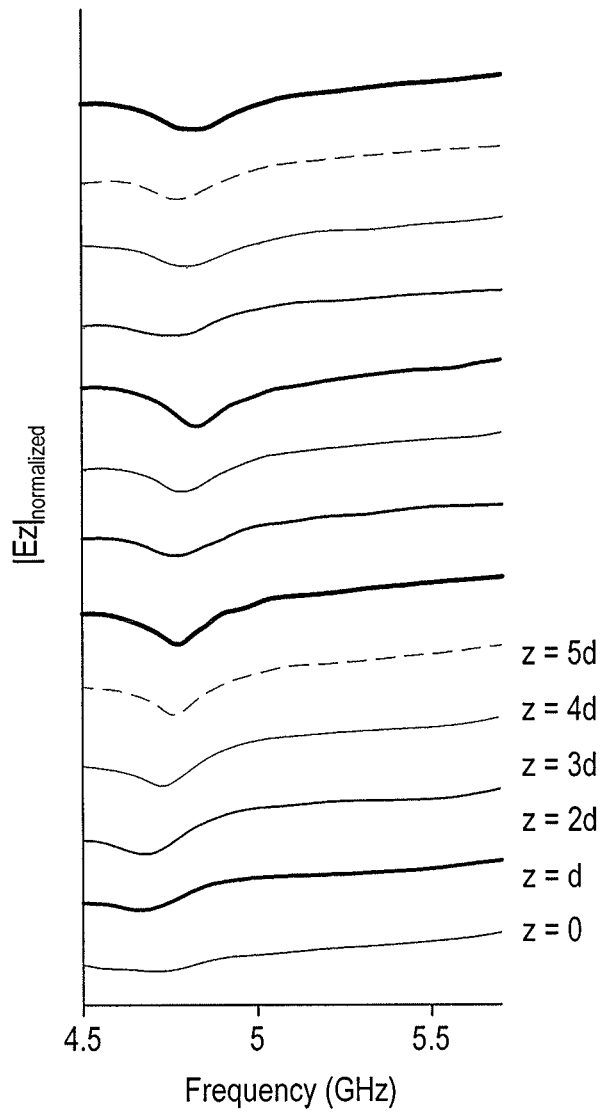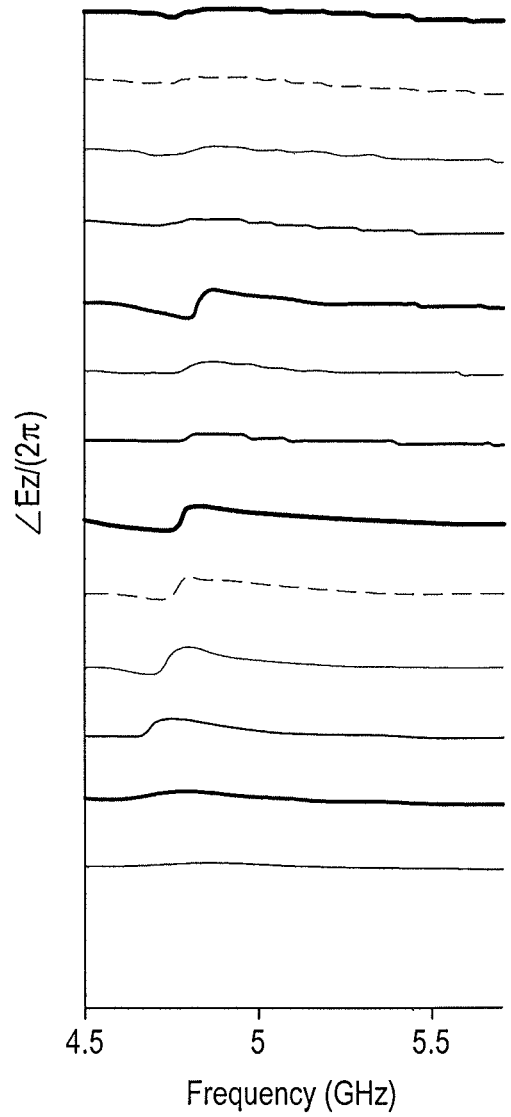
FIG. 7A
FIG. 7B

Frequency (GHz)
Transmission Amplitude

Frequency (GHz)
Transmission Phase

PLANT WATER SENSOR

BACKGROUND

1. Field

The disclosure of the present patent application relates to moisture meters, and more particularly to a plant water sensor for detecting plant moisture in real time.

2. Description of the Related Art

Monitoring growth conditions has been topic of research for better plant health and breeding. External conditions (such as weather, moisture, heat, and condition of the soil) affect the health of plants. Many techniques have been reported to monitor the health of plants. One approach is to measure the electrical parameters (resistance and capacitance) of leaves and stems through electric and electromagnetic measurement techniques and to correlate these quantities with plant water uptake. The basic problem associated with these sensors is the variation of resistance and capacitance with the change in temperature, solar activity, and water level. The changes due to temperature and solar activity have to be separately assessed, making the reliability and accuracy of these sensors very poor. Comparing the weight of fresh and dry plant tissues is another common method to measure water content in plants. The weight measuring methods are destructive in nature, and cannot provide instantaneous and continuous monitoring of the water content in living tissue.

Some non-destructive methods use microwave to terahertz radiation. These non-invasive methods are based on the fact that strong water absorption occurs at microwave and terahertz (THz) frequencies. In THz sensing, the common basis of the different methods is the strong absorption of THz and sub-THz waves by liquid water, thus allowing the continuous monitoring of plant water status over several days on the same sample. This technology is exceptionally expensive, and not suitable for commercial deployment at the farm level.

Another, low cost alternate to THz technology is a leaf-mounted thermal sensor arrangement for the measurement of water content. The main problem with the temperature-based sensors is deployment in severe conditions. For example, in the UAE environment, the ambient temperatures changes from 10° C. to 50° C., and humidity changes from 30% to 95%. These large changes in temperature and humidity will cause micro-heaters and thermocouples to be ineffective. In addition, the use of excessive heat at elevated temperatures will damage the physical tissue structure of the leaf. A particular problem with electronic moisture sensors as applied to plants is the plants is the level of electronic noise generated by or present in the outdoor environment.

Thus, a plant water sensor solving the aforementioned problems is desired.

SUMMARY

The plant water sensor determines moisture levels in plant leaves, stems and wood. The sensors described include several embodiments of the sensor, all of which estimate moisture levels by determining changes in the phase spectrum of an anomalous-phase resonator. Two embodiments include a planar transmitting antenna array with two rectangular square patches of different size and a detector. In a first embodiment, the detector is a dipole antenna centered and non-coplanar with the transmitting antenna array. In a second embodiment, the detector is a singular rectangular patch antenna coplanar with the transmitting antenna array. The third embodiment is similar to the second embodiment, but is formed on a flexible substrate, so that the sensor can be wrapped about a twig, branch or other plant structure, in a non-coplanar arrangement.

All embodiments are used in a plant water sensing system that includes at least one plant water sensor in conjunction with an RF signal generator and a signal processing circuit. The RF signal generator provides an RF signal that is applied to an input port of the sensor that is electrically connected to the two rectangular square patches of the planar transmitting antenna array. The signal processing circuit receives the RF response signal from an output port of the sensor that is electrically connected to the detector.

To compensate for temperature affects, a reference sensor may be integrated with an active sensor. The reference sensor uses a pre-calibrated hermitically sealed reference swab with water content corresponding to a healthy leaf of the plant species under test. The level of the water in the swab is fixed in such a way that response of a sensor loaded with fully healthy leaf and response of the reference sensor loaded with swab are exactly the same. This procedure calibrates out sensor frontend issues and also minute differences in the two electric paths. When both integrated sensors are in the field, the active sensor is loaded with a leaf under test. The temperature changes will affect the leaf and the swab in a similar way, therefore any first-order frequency shift due to the temperature will be automatically compensated. However, small second-order calibration errors may exist due to different masses of water in the leaf and in the swab. After calibration, the shift in the frequency between the two sensors (reference and active) can be attributed to the difference in leaf water content. This measured difference in frequency shift shows the relative difference in water content of the leaf under test to a fully healthy leaf.

These and other features of the present disclosure will become readily apparent upon further review of the following specification and drawings.

BRIEF DESCRIPTION OF THE DRAWINGS

FIG. 7A is a normalized plot of electric field magnitude versus frequency detected at various distances orthogonal to the transmitting patches in simulations using the plant water sensor of FIG. 1.

FIG. 7B is a plot of electric field phase versus frequency detected at various distances orthogonal to the transmitting patches in simulations using the plant water sensor of FIG. 1.

Similar reference characters denote corresponding features consistently throughout the attached drawings.

DETAILED DESCRIPTION OF THE PREFERRED EMBODIMENTS

The plant water sensor determines moisture levels in plant leaves, stems and wood. The sensors described include two embodiments of the sensor, both of which estimate moisture levels by determining changes in the phase spectrum of an anomalous phase resonator. The embodiments of the plant water sensor have two unequal patch antennas configured to combine near fields to generate a signal in the terahertz spectrum exhibiting the anomalous phase.

As described in our pending patent application entitled "Dielectric Constant Detection Method and Device Using Anomalous Phase Dispersion", published as U.S. Patent Publication No. 2017/0131334 on May 11, 2017 (two of the present inventors are co-inventors in the '334 application), the phrase "anomalous dispersion" refers to a phenomenon that has been observed in the scattering parameters of dielectric materials, and particularly in the $s_{21}$ parameter, also referred to as the transmission coefficient or transmission phase. In certain media, when used as a transmission line, the transmission phase exhibits a double slope reversal centered around the resonance frequency, which is in the terahertz range. This behavior is referred to as anomalous dispersion, or anomalous phase dispersion. The resulting resonant magnitude and phase spectra are connected through the well-known Kramers-Kronig relations. It has been shown by the present inventors that based on these relations, any material placed under the microstrip or above the microstrip can be completely characterized by the phase measurement in the anomalous dispersion due to the fact that the electric field is above and below the microstrip transmission line. The effect of the electric field on the dielectric constant and other dielectric properties allows monitoring for moisture levels and changes in water content, e.g., by the shift in the resonant frequency at which the double slope reversal occurs. The present plant water sensor shows that this phenomenon is not limited to transmission lines, but extends to signals radiated from an antenna array, permitting the construction of the present plant water sensors, which are relatively immune from the effects of environmental noise levels, since the phenomenon affects the phase of the signal.

Figure 1:
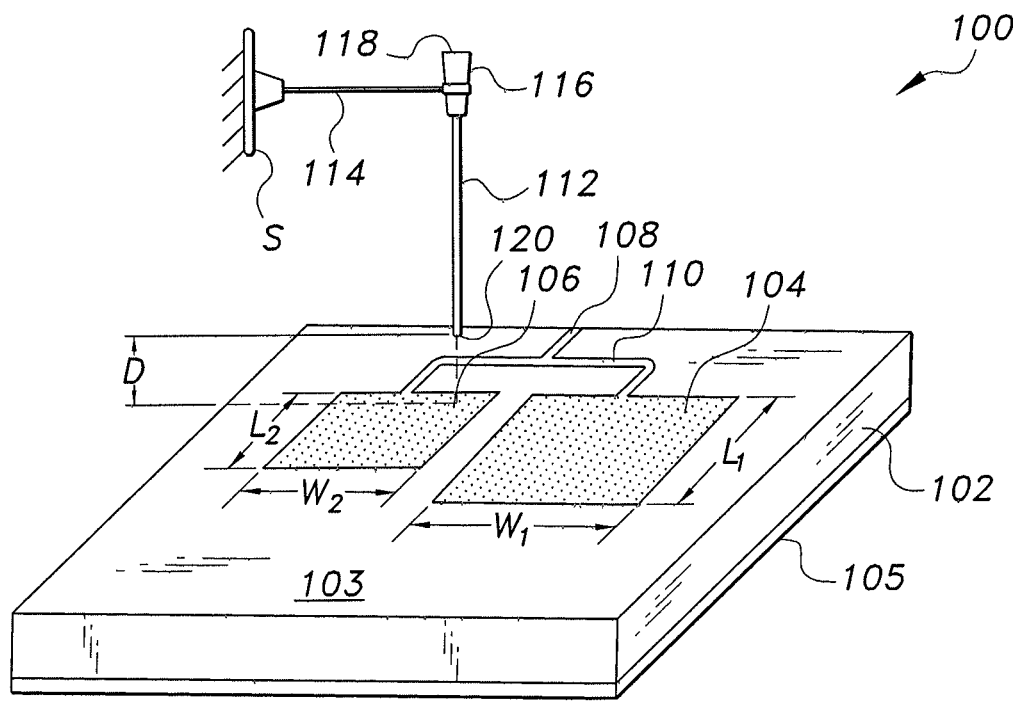
FIG. 1 is a perspective view of a first embodiment of the plant water sensor.
Figure 2:
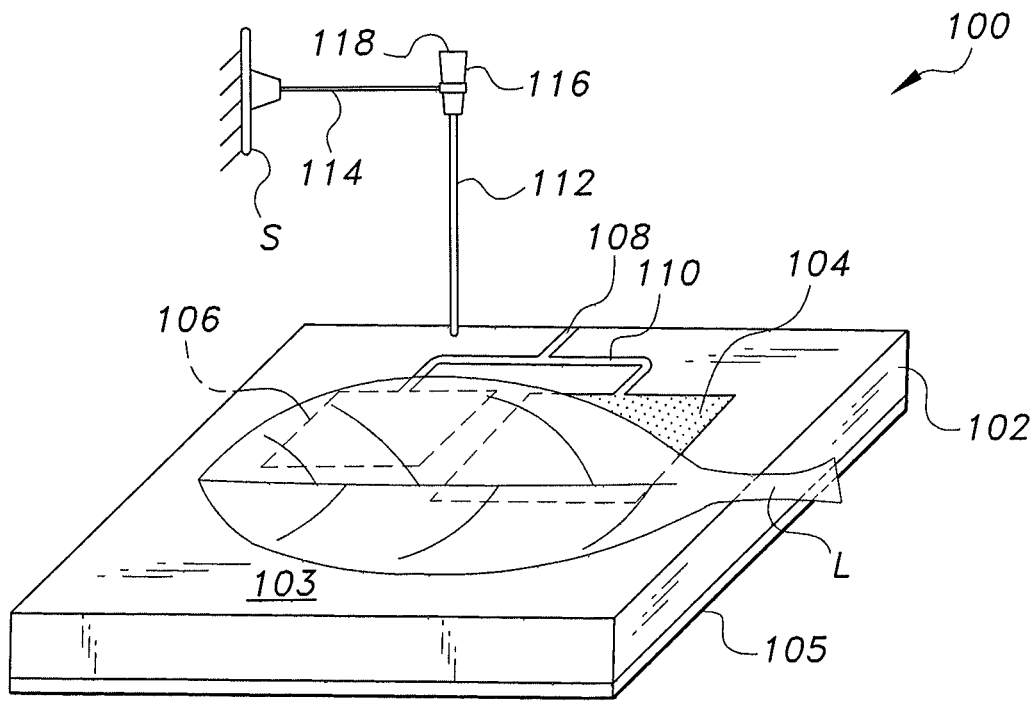
FIG. 2 is an environmental perspective view of the plant water sensor of FIG. 1, showing a leaf in position for sensing.

A first embodiment 100 of the plant water sensor is shown in FIGS. 1-2. The plant water sensor 100 includes an insulating substrate 102 having a first, substantially planar, top surface 103. An input port 108 is arranged along one edge of the surface 103 for receiving an RF transmit signal from a signal generator, as is explained below. A transmitting antenna array of the plant water sensor 100 includes a first, substantially rectangular, conductive transmitting patch antenna 104 having a length $L_1$ and a width $W_1$ and a second, substantially rectangular, conductive transmitting patch antenna 106 having a second length $L_2$ and a second width $W_2$. The two transmitting patch antennas 104 and 106 are intentionally slightly detuned (i.e., tuned to slightly different resonant frequencies) so that the signals will produced an enhanced absorption band when mixed. The length $L_1$ and the length $L_2$ are unequal and the width $W_1$ and the width $W_2$ are unequal, thereby generating the radiative anomalous phase by combining the near-fields of two unequal patch antennas. An input transmission line 110 electrically connects the input port 108 to the first 104 and second 106 transmitting patch antennas. The first patch antenna 104, the second patch antenna 106 and the input transmission line 110 are formed of a conductive material (preferably copper) that may be formed and shaped on the surface 103 of the insulating substrate 102, by conventional means such as depositing a conductor on an insulating substrate, and sequentially milling the conductive layer, for example using the MITS AUTOLAB milling machine. A layer 105 of conductive material (preferably copper) is preferably formed on the bottom surface of the insulating substrate 102, thereby forming a ground plane.

The detector or receiving antenna for the first embodiment 100 of the plant water sensor is a dipole antenna 112. The dipole antenna 112 is attached to a support S (which may be part of the plant being sensed) using a bracket 114 or other structure. The antenna 112 is isolated from the bracket using an insulator 116. An output port 118 is electrically connected to one end of the dipole antenna 112. The dipole antenna 112 arranged substantially perpendicular to the top surface 103 and centered with and spaced a distance D from the transmitting antenna array. Preferably the distance D is at least 4 cm, to best detect the radiative anomalous phase, as described further below.

In FIG. 2, a leaf L is shown in position on the sensor 100. It should be understood that the leaf L is exemplary, and the plant material may include living leaves, twigs, branches or trunks, as well as nonliving plant material such as wood, depending on any application where knowing the moisture content of the material is of importance. The leaf L overlies both the first 104 and second 106 transmitting patch antennas, thereby affecting the transmitted RF signal prior to reaching the dipole antenna 112, as is discussed further below.

Figure 3:
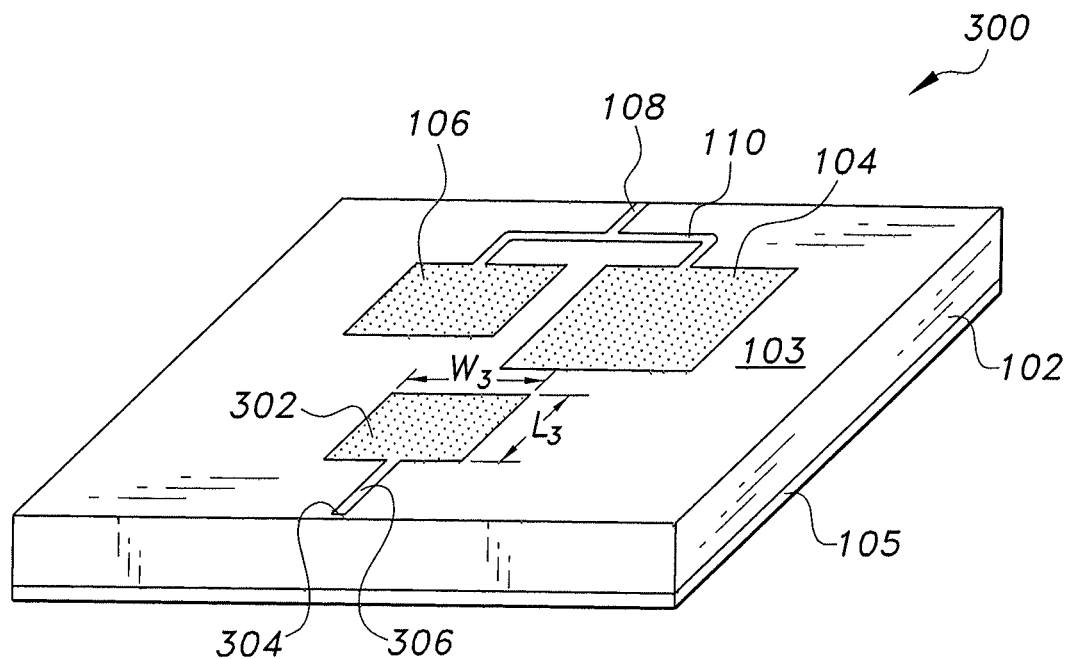
FIG. 3 is a perspective view of a second embodiment of the plant water sensor.
Figure 4:
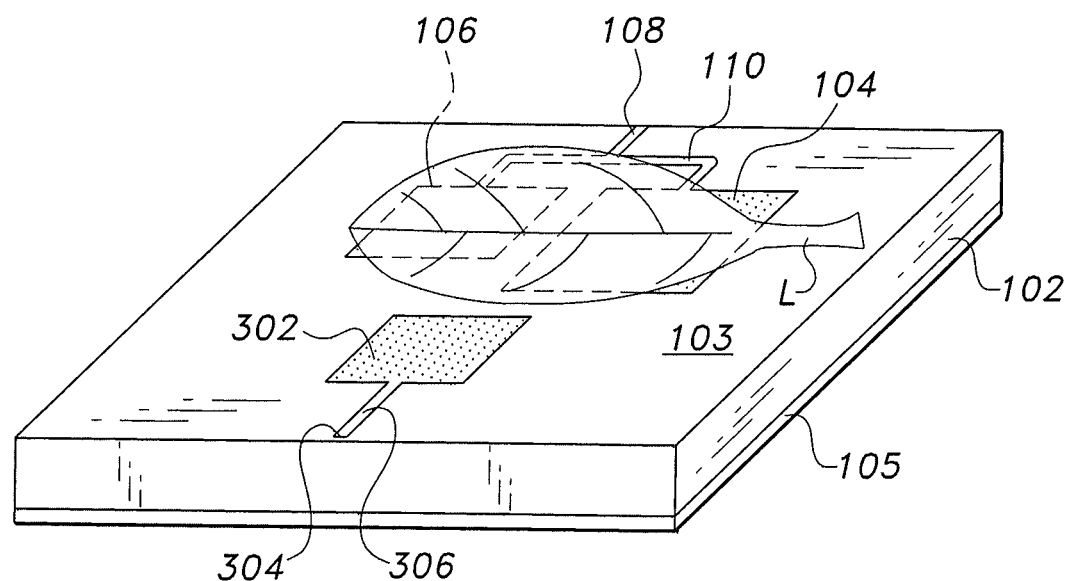
FIG. 4 is an environmental perspective view of the plant water sensor of FIG. 3, showing a leaf in position for sensing.

A second embodiment 300 of the plant water sensor is shown in FIGS. 3-4. The plant water sensor 300 includes a transmitting antenna array similar to the first embodiment 100, including an insulating substrate 102 having a first substantially planar top surface 103. An input port 108 is arranged along one edge of the surface 103, for receiving an RF transmit signal from a signal generator, as is explained below. A transmitting antenna array of the plant water sensor 300 includes a first substantially rectangular, conductive transmitting patch antenna 104 having a length $L_1$ and a width $W_1$ (see FIG. 1) and a second substantially rectangular, conductive, transmitting patch antenna 106 having a second length $L_2$ and a second width $W_2$ (see FIG. 1). The two patch antennas 104, 106 are slightly detuned, as explained above. The length $L_1$ and the length $L_2$ are unequal and the width $W_1$ and the width $W_2$ are unequal, thereby generating the radiative anomalous phase by combining the near-fields of two unequal patch antennas. An input transmission line 110 electrically connects the input port 108 to the first 104 and second 106 transmitting patch antennas. The first patch antenna 104, the second patch antenna 106 and the input transmission line 110 are formed of a conductive material (preferably copper). A layer 105 of conductive material (preferably copper) is preferably formed on the bottom surface of the insulating substrate 102, thereby forming a ground plane.

The detector or receiving antenna for the second embodiment 300 of the plant water sensor is a substantially rectangular, conductive, receiving patch antenna 302 on the top surface 103 of the insulating substrate 102 and having a length $L_3$ and a width $W_3$. An output transmission line 306 on the top surface 103 electrically connects the receiving patch antenna 302 to an output port 304.

In FIG. 4, a leaf L is shown in position on the sensor 300. As with the first embodiment, it should be understood that the leaf L is exemplary, and the plant material may include living leaves, twigs, branches or trunks, as well as nonliving plant material such as wood, depending on any application where knowing the moisture content of the material is of importance. The leaf L overlies both the first 104 and second 106 transmitting patch antennas, thereby affecting the transmitted RF signal, prior to reaching the receiving patch antenna 302, as is discussed further below. In this embodiment, the top surface 103 is planar and the first transmitting patch antenna 104, the second transmitting patch antenna 106 and the receiving patch antenna 302 are all coplanar.

Figure 5:
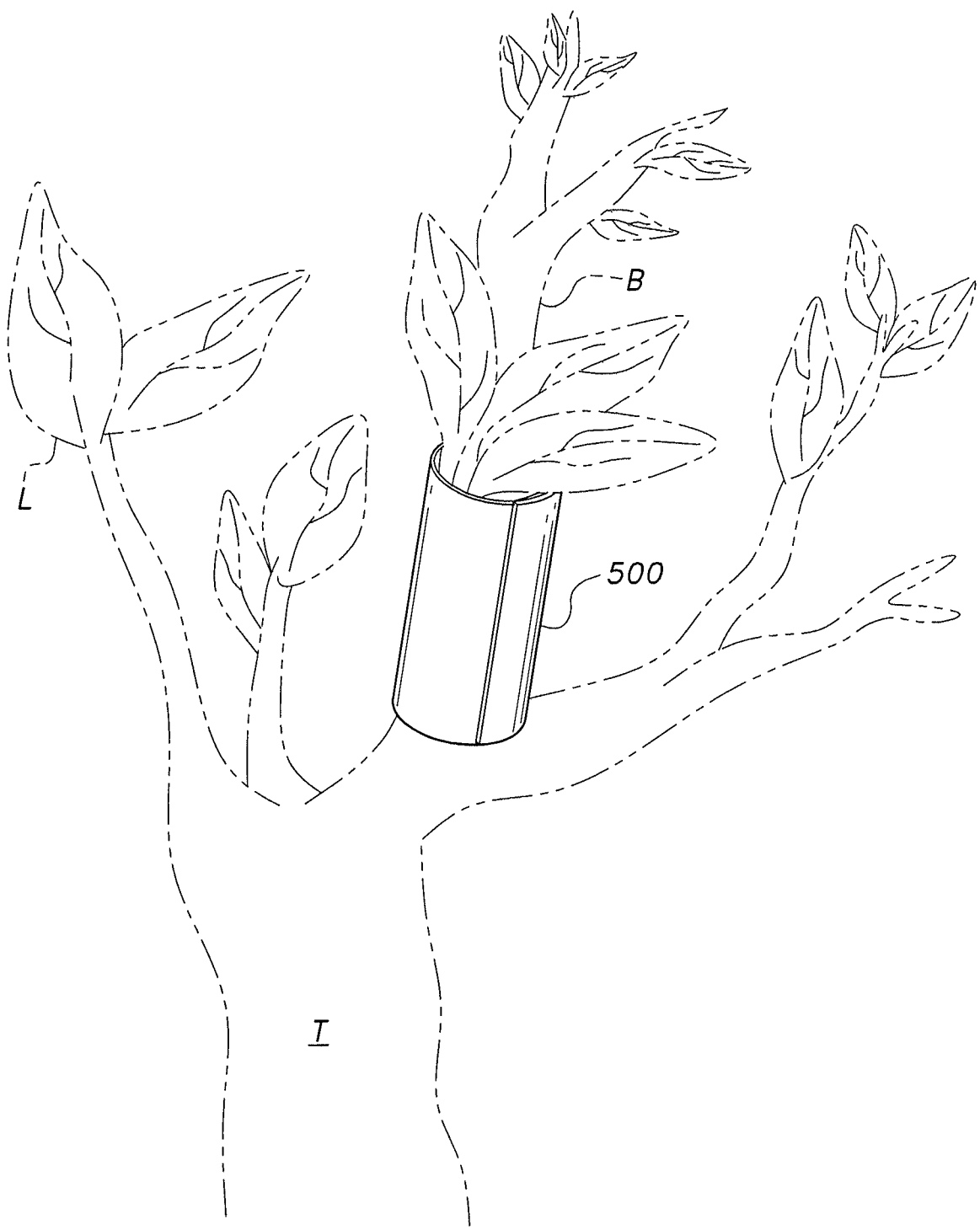
FIG. 5 is an environmental perspective view of a third embodiment of the plant water sensor, showing its application to a stem of a plant.

FIG. 5 illustrates a third embodiment of the plant water sensor 500. This embodiment includes all of the elements of the second embodiment, as described with respect to FIG. 3. However, in this embodiment, the insulating substrate 102, the first transmitting patch antenna 104, the second transmitting patch antenna 106 and the receiving patch antenna 302 are all formed of flexible materials, such that the sensor can be wrapped around itself to form a tube-shaped third embodiment of the plant water sensor 500 that is wrapped around the plant material of interest. As with the previous embodiments, the plant material may include living leaves, twigs, branches or trunks, as well as nonliving plant material such as wood, depending on any application where knowing the moisture content of the material is of importance.

Figure 6:
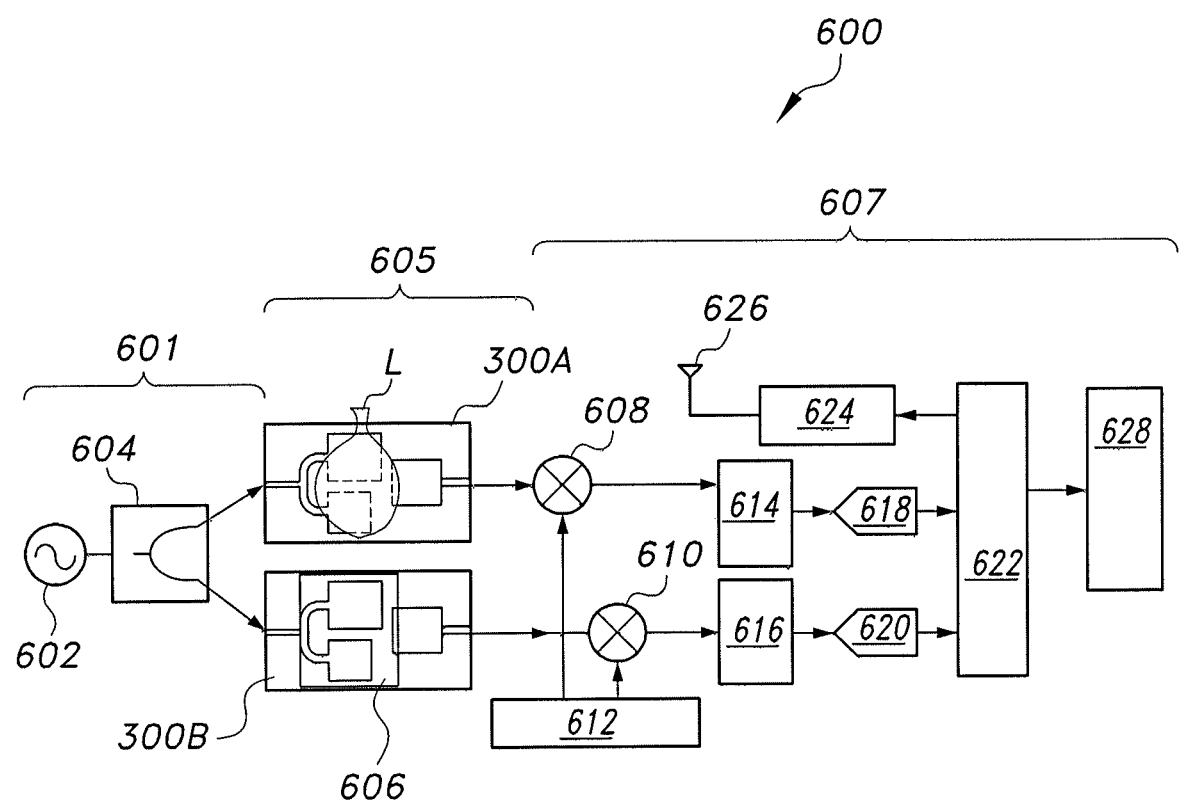
FIG. 6 is a block diagram of an electronic circuit for determining plant water amount using the plant water sensor.

FIG. 6 illustrates a system 600 for sensing plant water using a plant water sensor stage 605. The system includes a sensor source 601 having an RF signal generator 602 electrically connected to the input port of the plant water sensor stage 605 for supplying an input RF signal thereto and a sensor receiver 607 electrically connected to the output port of the plant water sensor stage 605 for receiving an output RF signal therefrom. In a preferred embodiment, the system is capable of compensating for temperature changes and has a plant water sensor stage 605 that includes a first plant water sensor 300A and a second reference sensor 300B. The first plant water sensor 300A is in close proximity to a plant sample L and the second reference sensor is in close proximity to a reference swab 606. In the preferred embodiment, the sensor source 601 further comprises a power divider 604 for connecting the signal generator 602 to the input ports of the first plant water sensor 300A and the second reference sensor 300B. Also in the preferred embodiment, the sensor receiver 607 includes a first mixer 608 that has an input connected to the output port of the first plant water sensor 300A to receive a plant water signal, and a second mixer 610 that has an input connected to the output port of the second reference sensor 300B to receive a reference signal. A frequency synthesizer 612 provides a mixing frequency to the first 608 and second 610 mixers and the mixers provide sum, difference and original frequency outputs as is known in the art. A first amplification and filtering circuit 614 is connected to the output of the first mixer 608, to filter and amplify the difference signal from the first mixer 608. A second amplification and filtering circuit 616 is connected to the output of the second mixer 610, to filter and amplify the difference signal from the first mixer 610. A first analog-to-digital converter 618 is connected to the output of the first amplification and filtering circuit 614 to provide a digital signal to a processor 622 that is representative of the moisture level in the plant sample L.

A second analog-to-digital converter 620 is connected to an output of the second amplification and filtering circuit 616 to provide a digital signal to the processor 622 that is representative of the moisture level in the reference swab 606. The reference swab 606 has a moisture level equal to the desired moisture level in a plant sample of the same species. The processor 622 includes the required memory, software and auxiliary devices to determine and report plant water/moisture levels based on the received plant water signal and the reference signal. As with many computer systems, a video display 628 is provided to display results locally, as well as a wireless communications module 624 for communicating remotely via an antenna 626. The preferred wireless communication protocol is Bluetooth.

FIG. 7A is a normalized plot of electric field magnitude versus frequency detected at various distances orthogonal to the transmitting patches in simulations using the plant water sensor of FIGS. 1-2, while FIG. 7B is a plot of electric field phase versus frequency detected at various distances orthogonal to the transmitting patches in simulations using the plant water sensor of FIGS. 1-2. The plots were created using the full-wave simulator COMSON. The simulated z-directed electric field magnitude ($|E_z|$) and phase ($<E_z$) plots for the out-of-plane or non-coplanar detection are shown in FIGS. 7A and 7B, respectively. Anomalous dispersion is evident in the phase plots obtained at a distance of 4 d (4 cm) and above.

Figure 8A:
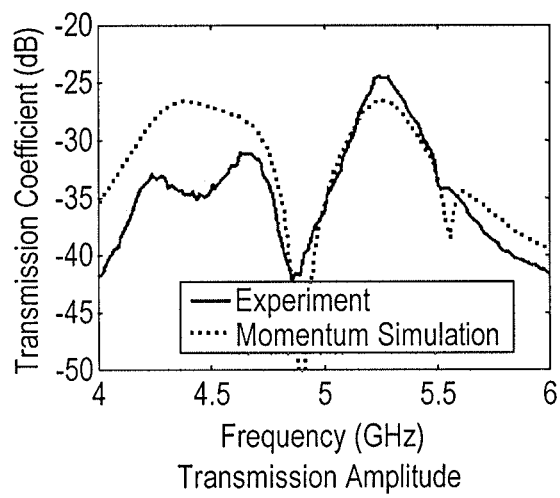
FIG. 8A is a plot of electric field magnitude versus frequency detected by the coplanar receiver patch in simulations using the plant water sensor of FIG. 3.
Figure 8B:
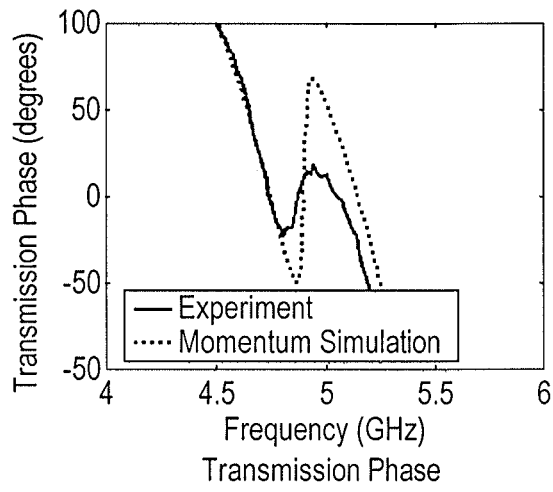
FIG. 8B is a plot of electric field phase versus frequency detected by the coplanar receiver patch in simulations using the plant water sensor of FIG. 3.

The second embodiment of the plant water sensor 300 was simulated using the Agilent Momentum full wave simulator. FIG. 8A is a plot of electric field magnitude versus frequency detected by the coplanar receiver patch in simulations using the plant water sensor of FIGS. 3-4, while FIG. 8B is a plot of electric field phase versus frequency detected by the coplanar receiver patch in simulations using the plant water sensor of FIGS. 3-4. The dual-patch array was excited with a Rohde and Schwarz ZVL13 Vector Network Analyzer (VNA). The fields were detected at the output port 304 of the receiving patch antenna 302. As shown in FIGS. 7A and 7B, two resonant regions appear in the amplitude spectrum with an absorption band in the middle.

In addition to sensing moisture levels in plants, the sensors 100 and 300 may be used to sense moisture levels in a block of wood by placing the block of wood over the transmitting antennas in place of the leaf in FIGS. 2 and 4, respectively. Absolute water levels may be detected by calibrating the resonant frequency at which anomalous phase dispersion occurs for samples of known content, and relative changes in moisture levels may be detected by a change in the resonant frequency at which anomalous phase dispersion occurs.

It is to be understood that the plant water sensor is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A plant water sensor that determines moisture through anomalous phase measurement, comprising:
   an insulating substrate having a first surface;
   an input port on the first surface adapted for connection to a signal source;
   a transmitting antenna array having a first substantially rectangular, conductive transmitting patch antenna on the first surface and a second substantially rectangular, conductive, transmitting patch antenna on the first surface, the first and second transmitting patch antennas being tuned to different resonant frequencies, wherein the first patch antenna has a first length and a first width, the second patch antenna has a second length and a second width, the first length and the second length being unequal and the first width and the second width being unequal, the insulating substrate and the first and second transmitting patch antennas defining a sample platform for receiving a sample of plant material to be tested for water content;

a microstrip input transmission line on the first surface electrically connecting the input port to the first and second transmitting patch antennas, thereby splitting an input signal between the first and second transmitting antennas;

a receiving antenna, wherein the first and second transmitting patch antennas and the receiving antenna are positioned and configured so that near field emissions of the same input signal from the first and second transmitting antennas are mixed at the receiving antenna, thereby forming an output signal exhibiting anomalous phase dispersion correlated with water content of the sample of plant material on the sample platform; and an output port electrically connected to the receiving antenna, the output port being adapted for connection to a signal analyzer circuit.

2. The plant water anomalous Phase sensor as recited in claim 1, wherein the receiving antenna comprises a dipole antenna disposed in a plane orthogonal to the first and second transmitting antennas, and is centered with and spaced a distance D from the transmitting antenna array.

3. The plant water anomalous Phase sensor as recited in claim 2, wherein the distance D is at least 4 cm.

4. The plant water anomalous Phase sensor as recited in claim 1, wherein the receiving antenna comprises:

a substantially rectangular, conductive, receiving patch antenna on the first surface coplanar with the first and second transmitting patch antennas, the receiving patch antenna having a third length and a third width; and a microstrip output transmission line on the first surface electrically connecting the receiving patch antenna to the output port.

5. The plant water anomalous Phase sensor as recited in claim 1, wherein the insulating substrate, the first transmitting patch antenna, the second transmitting patch antenna and the receiving patch antenna are all formed of flexible material, such that the sensor can be wrapped around itself to form a tube around the sample of plant material.

6. A system for sensing plant water content, comprising:
at least one pant water sensor having:
an insulating substrate having a first surface;
an input port on the first surface;
a transmitting antenna array including a first conductive transmitting patch antenna on the first surface and a second conductive transmitting patch antenna on the first surface, the first and second transmitting patch antennas being detuned, the substrate and the transmitting antennas being adapted for receiving a sample of plant material to be tested for water content extending across the transmitting antennas;
an input transmission line on the first surface electrically connecting the input port to the first and second transmitting patch antennas in order to split an input signal between the first and second transmitting antennas;

a receiving antenna disposed for receiving superimposed signals from the first and second detuned transmitting antennas, the receiving antenna being disposed on the first surface coplanar with the first and second patch antennas, wherein each of the first and second patch antennas and receiving antenna have distinct configurations;
an output port electrically connected to the receiving antenna;
an output transmission line on the first surface electrically connecting the receiving antenna to the output port;
a sensor source having an RE signal generator electrically connected to the input port for supplying an input RE signal thereto; and a sensor receiver electrically connected to the output port for receiving an output RF signal therefrom.

7. The system for sensing plant water as recited in claim 6, wherein:
the at least one plant water sensor comprises a first plant water sensor and a second reference sensor, the first plant water sensor being in close proximity to a plant sample and the second reference sensor being in close proximity to a reference swab;
the sensor source further comprises a power divider for connecting the signal generator to the input ports of the first plant water sensor and the second reference sensor, and
the sensor receiver comprises:
a first mixer connected to the output port of the first plant water sensor
a second mixer connected to the output port of the second reference sensor;
a frequency synthesizer connected to the first and second mixers;
a first amplification and filtering circuit connected to an output of the first mixer;
a second amplification and filtering circuit connected to an output of the second mixer;
a first analog-to-digital converter connected to an output of the first amplification and filtering circuit;
a second analog-to-digital converter connected to an output of the second amplification and filtering circuit; and
a processor connected to an output of the first analog-to-digital converter and an output of the second analog-to-digital converter.

8. The system for sensing plant water as recited in claim 7, further comprising a video display connected to the processor.

9. The system for sensing plant water as recited in claim 7, further comprising a wireless communication module connected to the processor.

10. The system for sensing plant water as recited in claim 6, wherein the first surface is planar and the first transmitting patch antenna, the second transmitting patch antenna and the receiving patch antenna are all coplanar on the first surface.

11. The system for sensing plant water as recited in claim 6, wherein the insulating substrate, the first transmitting patch antenna, the second transmitting patch antenna and the receiving antenna are all formed of flexible material, such that the sensor can be wrapped around itself to form a tube.

12. A method of sensing water content in plant material, comprising the steps of:
extending a sample of plant material across a pair of detuned microstrip patch antennas;
inputting a signal split between the pair of detuned microstrip patch antennas for transmission therefrom;

receiving superimposed near field signals transmitted from the pair of detuned microstrip patch antennas, the superimposed near field signals exhibiting anomalous phase dispersion;

analyzing the received superimposed near field signals to determine the frequencies at which reversal of slope in the phase of the near field signals occurs;

computing resonant frequency of the received superimposed near field signals from the frequencies at which reversal of slope in the phase of the near field signals occurs; and comparing the computed resonant frequency with the resonant frequencies of similar calibrated plant samples of known water content to determine the water content of the sample plant material.

13. The method of sensing water content in plant material according to claim 12, further comprising the steps of:

continuously monitoring the received superimposed near field signals; and signaling a change in water content when the computed resonant frequency changes.

* * * * *